United States Patent [19]

Haydock et al.

[11] 4,055,595

[45] Oct. 25, 1977

[54] SUBSTITUTED ARYLOXY-3,3,3-TRIFLUORO-2-PROPIONIC ACIDS, ESTERS AND SALTS THEREOF

[75] Inventors: David Bryan Haydock; Thomas Patrick Cunningham Mulholland; Jeffrey Meyrick Thorp, all of Macclesfield, England

[73] Assignee: Imperial Chemical Industries Limited, London, England

[21] Appl. No.: 630,685

[22] Filed: Nov. 10, 1975

[30] Foreign Application Priority Data

Dec. 6, 1974 United Kingdom ............... 52829/74

[51] Int. Cl.² ..................... C07C 65/14; C07C 65/02; C07C 69/76
[52] U.S. Cl. .......................... 260/520 B; 260/295 CA; 260/448 AD; 260/463; 260/501.1; 260/520 C; 260/559 B; 260/559 D; 424/300; 424/301; 424/308; 424/309; 424/316; 424/317; 424/324; 260/521 H; 560/56; 560/60; 560/62; 560/59; 560/63

[58] Field of Search ......... 260/520 B, 501.1, 448 AD, 260/521 H, 473 F, 473 A

[56] References Cited

U.S. PATENT DOCUMENTS

| 3,347,910 | 10/1967 | Bolhofer et al. | 260/520 C |
| 3,363,003 | 1/1968 | Bolhofer | 260/520 C |
| 3,549,690 | 12/1970 | Leigh et al. | 260/473 A |
| 3,642,869 | 2/1972 | Narayanan et al. | 260/520 C |
| 3,721,703 | 3/1973 | Nahm et al. | 260/520 C |
| 3,740,437 | 6/1973 | Harrison et al. | 260/520 C |
| 3,954,442 | 5/1976 | Becker et al. | 260/520 C |

Primary Examiner—Norman Morgenstern
Attorney, Agent, or Firm—Cushman, Darby & Cushman

[57] ABSTRACT

Derivatives of 2-hydroxy-3,3,3-trifluoro-2-(alkyl or trifluoromethyl)propionic acid bearing a phenyl or naphthyl group linked to the 2-hydroxy group either directly or via an intermediate methylene group. The compounds reduce the concentrations of cholesterol, total esterified fatty acids or fibrinogen in the blood plasma of test animals and some compounds show anti-arthritic properties.

8 Claims, No Drawings

SUBSTITUTED ARYLOXY-3,3,3-TRIFLUORO-2-PROPIONIC ACIDS, ESTERS AND SALTS THEREOF

This invention relates to fluorinated compounds and in particular it relates to fluorinated compounds which have a desirable influence on at least one of the factors involved in atherosclerotic disease. In addition, some of the fluorinated compounds shown anti-arthritic properties.

According to the invention there is provided a fluorinated compound of the formula:

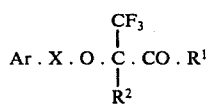

wherein Ar is a phenyl or naphthyl radical which may optionally bear as substituent a halogen atom or an alkyl or alkoxy radical of 1–4 carbon atoms, or a phenyl or phenoxy radical which may itself bear as substituent a halogen atom or an alkyl or alkoxy radical of 1–4 carbon atoms; X is a group of the formula —O.CH$_2$— or —CH$_2$— or a direct link between the group Ar and the adjacent oxygen atom; R$^1$ is a hydroxy, amino or dimethylamino radical, or an alkoxy radical of 1–6 carbon atoms optionally substituted by a carbamoyl radical or an N,N-dialkylcarbamoyl or dialkylamino radical in which the alkyl radicals are of 1–6 carbon atoms, a pyridyl radical, a halophenoxy radical or a group of the formula Ar.X.O.C(CF$_3$)R$^2$.CO.O—; and R$^2$ is a hydrogen atom or an alkyl radical of 1–4 carbon atoms or a trifluoromethyl radical; or, for a compound wherein R$^1$ is a hydroxy radical, a pharmaceutically acceptable base addition salt thereof.

It will be observed that those compounds of formula I wherein R$^2$ is other than a trifluoromethyl radical contain an asymmetric carbon atom and that accordingly, such compounds can be isolated in a racemic form and two optically active forms. This specification is addressed to the racemic form of the compounds of formula I wherein R$^2$ is other than a trifluoromethyl radical and any optical isomer which shows the above useful properties; it being a matter of general knowledge how to resolve the racemic form and how to determine the biological properties of the optical isomers.

A particularly suitable value for a substituent which may be present on the phenyl or naphthyl radical Ar is, for example a fluorine, chlorine, bromine or iodine atom, a methyl or methoxy radical or a phenyl or phenoxy radical optionally bearing a fluorine, chlorine, bromine or iodine atom or a methyl or methoxy radical. Specific values for Ar are, for example, a phenyl, 4-fluorophenyl, 4-chlorophenyl, 4-methoxyphenyl, 4-biphenylyl, 4-phenoxyphenyl, 4-(4-chlorophenyl)phenyl, 1-naphthyl, 2-naphthyl, 4-chloro-1-naphthyl, 2-methyl-1-naphthyl, 6-chloro-2-naphthyl or 6-methoxy-2-naphthyl radical.

A particularly suitable value for R$^1$ when it is an alkoxy radical of 1-6 carbon atoms is, for example, a methoxy, ethoxy, propoxy or butoxy radical, and a particularly suitable value for a substituent which may be present on an alkoxy radical when it is a value for R$^1$ is, for example, a carbamoyl, N,N-dimethylcarbamoyl, dimethylamino, diethylamino, 3-pyridyl or a 4-chlorophenoxy radical. Specific values for R$^1$ when it is a substituted alkoxy radical are, for example, a 3-(N,N-dimethylcarbamoyl)propoxy, 2-(diethylamino)ethoxy, 3-pyridylmethoxy or 2-(4-chlorophenoxy)-2-methylpropoxy radical, or the group Ar.X.O.C(CF$_3$)R$^2$.CO.O.(CH$_2$)$_3$O—, i.e. the group forming a diester with 1,3-propanediol.

A particularly suitable value for R$^2$ when it is an alkyl radical of 1-4 carbon atoms is, for example, a methyl radical.

Particularly suitable base addition salts of a compound wherein R$^1$ is a hydroxy radical are, for example, alkali metal and alkaline earth metal salts, for example sodium, potassium, calcium or magnesium salts, aluminium salts, for example an aluminium hydroxide di-salt, or salts with organic bases, for example ethyl nicotinate, ethyl 5-fluoronicotinate, nicotinyl alcohol, 2-aminoethyl nicotinate or 2-diethylaminoethyl nicotinate.

A particular group of compounds of formula I comprises those compounds wherein X is a methylene (—CH$_2$—) group and R$^2$ is a trifluoromethyl radical. Preferred among these compounds are those wherein Ar is a phenyl radical optionally substituted by a halogen atom or a halophenyl radical, or Ar is a naphthyl radical optionally substituted by a halogen atom or an alkyl or alkoxy radical of 1-4 carbon atoms.

A second particular group of compounds of formula I comprises those compounds wherein X is a direct link and R$^2$ is a trifluoromethyl radical. Preferred among these compounds are those wherein Ar is a phenyl radical optionally substituted by a halogen atom, an alkyl or alkoxy radical of 1-4 carbon atoms, or a phenyl, phenoxy or halophenyl radical, or Ar is a naphthyl radical.

A third particular group of compounds of formula I comprises those compounds wherein X is a direct link and R$^2$ is a methyl radical. Preferred among these compounds are those wherein Ar is a phenyl radical optionally substituted by a halogen atom, or a phenyl, phenoxy or halophenyl radical.

A fourth particular group of compounds of formula I comprises those compounds wherein X is a methylene (—CH$_2$—) group and R$^2$ is a methyl radical. Preferred among these compounds are those wherein Ar is a phenyl radical optionally substituted by a halogen atom or a halophenyl radical, or Ar is a naphthyl radical optionally substituted by a halogen atom or an alkyl or alkoxy radical of 1-4 carbon atoms. Particularly preferred are those compounds wherein Ar is a phenyl radical substituted by a halophenyl radical, for example a 4-chlorophenyl radical, or Ar is a naphthyl radical optionally substituted by a halogen atom, for example a chlorine atom.

In each of the above groups, R$^1$ may be as stated above, but preferred values for R$^1$ are a hydroxy or amino radical or an alkoxy radical of 1-6 carbon atoms, for example a methoxy or ethoxy radical.

Specific compounds of formula I are set out in the Examples, and of these, the following compounds are preferred:

2-[4-(4-chlorphenyl)benzyloxy]-3,3,3-trifluoro-2-methylpropionic acid, 2-(4-chloro-1-naphthylmethoxy)-3,3,3-trifluoro-2-methylpropionic acid, 2-(2-naphthylmethoxy)-3,3,3-trifluoro-2-methyl-propionic acid, 2-(1-naphthylmethoxy)-3,3,3-trifluoro-2-methyl-propionic acid, 2-[4-(4-chlorophenyl)benzyloxy]-3,3,3-trifluoro-2-trifluoromethylpropionic acid 2-(2-naphthylmethoxy)-3,3,3-trifluoro-2-trifluoromethylpropionic acid.

The compounds of formula I may be made by processes which are applicable to the manufacture of analogous compounds. Such processes are exemplified by the following in which Ar, X, $R^1$ and $R^2$ have the meanings stated above:

a. Reacting a compound of the formula:

$$Ar.X.Z \qquad \qquad II$$

wherein when X is other than a direct link, Z is a halogen atom or an alkane- or arene- sulphonyloxy group, for example a chlorine or bromine atom or a methanesulphonyloxy or toluene-p-sulphonyloxy group, and when X is a direct link, Z is an aryliodonium or 2-thienyliodonium radical, with a salt of the formula:

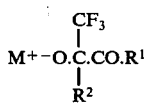

wherein $M^+$ is a metal cation, and a preferred value for $R^1$ is an amino or dimethylamino radical, or an alkoxy radical optionally substituted as stated above.

The salt of formula III may be pre-formed from a hydroxy compound of formula IV and a base, which is preferred, or it may be formed in the reaction by using the hydroxy compound of the formula:

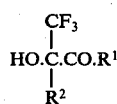

as starting material and carrying out the reaction in the presence of a base. A convenient value for M is an alkali metal, for example sodium or potassium, and a convenient base is, for example, sodium or potassium hydride.

When X is other than a direct link, the reaction is conveniently carried out at ambient temperature for an extended period in an inert solvent, for example dimethylformamide, and when X is a direct link, the reaction is conveniently carried out by heating a salt of the cation of the formula:

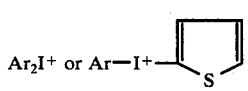

for example a chloride, bromide, acetate, hydrogen sulphate or trifluoroacetate, with an alkali metal salt of formula III either in the absence of a solvent or in an inert high boiling solvent, for example xylene or toluene, or initially in the absence of a solvent and subsequently in the presence of a solvent.

b. For a compound of formula I wherein $R^1$ is a hydroxy radical, hydrolysing an ester of the formula:

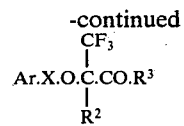

wherein $R^3$ is an alkoxy radical of 1-6 carbon atoms.

The hydrolysis is conveniently carried out, for example, by reacting the ester of formula V with a base, for example sodium hydroxide or potassium hydroxide, in an inert solvent, for example ethanol or methanol optionally mixed with water. $R^3$ is preferably a methoxy or ethoxy radical, and the hydrolysis is conveniently carried out at room temperature for a period of 1½ hours to 3 days. A short hydrolysis time, for example 2-5 hours, is effective in many cases, but a longer time may often be employed.

c. For a compound of formula I wherein $R^1$ is an amino radical, hydrolysing a nitrile of the formula:

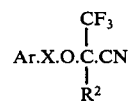

The hydrolysis is conveniently carried out, for example, by reacting the nitrile of formula VI with a base, for example sodium hydroxide or potassium hydroxide, in an inert solvent, for example methanol or ethanol optionally mixed with water. The hydrolysis is conveniently carried out at room temperature for a period of several days, or a shorter period at 60°-80° C.

d. For a compound of formula I wherein $R^1$ is an amino or dimethylamino radical, reacting ammonia or dimethylamine with an acid halide of the formula:

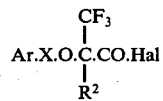

wherein Hal stands for a halogen atom, preferably a chlorine or bromine atom.

The reaction is conveniently carried out by reacting aqueous ammonia or aqueous dimethylamine with the acid halide at ambient temperature, but other solvents may be employed and the reaction mixture may be heated.

e. For a compound of formula I wherein $R^1$ is an alkoxy radial optionally substituted as defined above, esterifying the corresponding acid of formula I wherein $R^1$ is a hydroxy radical.

The esterification may be conveniently carried out using the corresponding diazoalkane, particularly when $R^1$ is a methoxy radical; by reacting the acid with the alcohol in the presence of an acid catalyst; or by reacting an acid halide, especially an acid chloride or bromide, or anhydride with the alcohol in the presence of a base, for example pyridine, triethylamine or N,N-dimethylaniline.

f. For a compound wherein $R^1$ is a dimethylamino radical and $R^2$ is hydrogen, heating a compound of the formula:

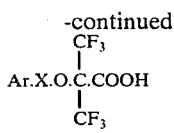

with dimethylformamide and sodium hydride.

The heating is conveniently carried out at 100° C. for 12–24 hours.

When an optical isomer of a compound of formula I, wherein $R^2$ is other than a trifluoromethyl radical, is desired, the corresponding racemic compound may be resolved or one of the above processes may be carried out using an optically active starting material. For example an acid of formula I wherein $R^1$ is a hydroxy radical may be resolved by fractional crystallization of a salt formed with an optically active base, for example (+)- or (−)-ephedrine, from a solvent, for example toluene. The optically active acid may then be recovered from the salt in the usual way and esterified to give an optically active ester.

As indicated above, the compounds of the invention are able to exert a desirable influence on one or more of the factors involved in atherosclerotic disease. These factors are elevated concentrations of cholesterol, total esterified fatty acids and fibrinogen in the blood plasma, and the compounds of the invention are capable of lowering the concentration of at least one member of the above group of blood plasma components in warm blooded animals. This property is demonstrated in standard tests by the effect of the compounds in lowering the concentration of the relevant blood plasma component to at least 80% of the control value when administered orally to rats over a period of 7 to 14 days, or by their activity, or that of the corresponding acid, in vitro, in displacing thyroxine from human albumin when present in an equimolar amount relative to the albumin. In this test an increase in the amount of unbound thyroxine similar to that produced by 2-(4-chlorophenoxy)-2-methylpropionic acid is considered to represent highly significant activity. In these tests, no overt toxic effects were noticed at the active dose.

When used to lower the concentrations of the above blood plasma components in warm blooded animals, the compounds may be administered in the diet at concentrations from 0.005% to 0.2%, or they may be administered orally in the form of a pharmaceutical composition so that a daily dose of from 5 mg./kg. to 200 mg./kg. is received by the host. In man this is equivalent to a dose of 0.1 g. to 2 g. per day given in divided doses.

The anti-arthritic properties of some of the compounds of formula I are demonstrated by their effect in inhibiting the increase in the thickness of a rat's foot injected with dead tubercle bacilli when administered over 21 days, essentially according to the standard test of Newbould (Brit. J. Pharmacol., 1963, 21, 127–136), and also their effect in inhibiting the increase in the concentration of $\alpha_1$ acid glycoprotein in the blood serum of the rats used in this test. Compounds of formula I wherein X is a methylene (—$CH_2$—) group or a direct link, $R^2$ is a methyl or trifluoromethyl radical and Ar is a phenyl radical substituted in the 4-position by a halophenyl radical, particularly a 4-chlorophenyl radical, or Ar is a naphthyl radical substituted by a halogen atom, particularly a chlorine atom, show activity without overt toxic effects at a daily dose of 50 mg./kg. or less. The preferred compound is 2-[4-(4-chlorophenyl)-benzyl-oxy]-3,3,3-trifluoro-2-methylpropionic acid or a salt thereof.

When used to produce anti-arthritic effects in warm blooded animals, those of the compounds of formula I defined immediately above may be administered orally at a daily dose of from 1 to 100 mg./kg. In man this is equivalent to a total daily dose of from 25 to 1000 mg. given, if necessary, in divided doses.

The compounds of the invention may be administered in the form of pharmaceutical compositions and according to a further feature of the invention there is provided a pharmaceutical composition which comprises a fluorinated compound of the invention in pharmaceutically acceptable form.

By "pharmaceutically acceptable form" is meant either a pharmaceutical preparation in which the compound is associated with a pharmaceutically acceptable diluent, or a pharmaceutical preparation, for example a capsule, in which the compound is confined in a unit dosage form without necessarily being associated with a diluent.

Preferred pharmaceutically acceptable forms are those suitable for oral administration, for example tablets, capsules, suspensions or solutions, which may be obtained by conventional methods and, if desired, by using conventional diluents or excipients. Dosage forms should contain from 50 mg. to 500 mg. of fluorinated compound per dosage unit.

Compositions intended for use in the treatment of atherosclerotic disease may also contain other agents which can have a beneficial effect on the disease or associated conditions, for example nicotinyl alcohol, nicotinic acid or a salt thereof, raubasine, vitamin E, an anion exchange resin, for example cholestyramine, colestipol or a dialkylaminoalkyl derivative of a cross-linked dextran, or a calcium or magnesium salt, or metformin or phenformin.

Compositions intended for use in the treatment of arthritis may also contain other agents having antiinflammatory or analgesic activity, for example, aspirin, paracetamol, codeine, chloroquine, phenylbutazone, D-penicillamine, indomethacin, ibuprofen, ketoprofen or naproxen, or an anti-inflammatory steroid, for example prednisolone, or a uricosuric agent, for example probenecid.

The invention is illustrated but not limited by the following Examples:-

EXAMPLE 1

Ethyl 2-hydroxy-3,3,3-trifluoro-2-trifluoromethylpropionate (12.0 g.) is added dropwise at ambient temperature to a stirred mixture of sodium hydride (2.4 g. of a 60% dispersion in oil) and dimethylformamide (100 ml.). The mixture is stirred for 4 hours, 4-chlorobenzyl chloride (8.4 g.) is added, and the stirring is continued for 6 days. The mixture is filtered, and the filtrate is evaporated in vacuo. The residue is fractionally distilled at 0.1 mm. pressure, collecting the fraction, (9.9 g.) b.p. 78°–80° C., m.p. 32°–33° C, which is crystallized from pentane to give ethyl 2-(4-chlorobenzyloxy)-3,3,3-trifluoro-2-trifluoromethylpropionate, m.p. 33° C.

The ethyl 2-hydroxy-3,3,3-trifluoro-2-trifluoromethylpropionate used as starting material may be obtained as follows:-

A mixture of 2-hydroxy-3,3,3-trifluoro-2-trifluoromethylpropionitrile sodium salt (200 g.) and concentrated sulphuric acid (500 ml.) is heated under reflux for 6 hours. The mixture is distilled at ambient pressure and the fraction (180 g.) which sublimes and distills at 150°–160° C. is collected. It consists of 2-hydroxy-3,3,3-trifluoro-2-trifluoromethylpropionic acid, pure enough for use, but which may be further purified by crystallization from a mixture of toluene and light petroleum (b.p. 60°–80° C.), forming hygroscopic crystals m.p. 76°–82° C.

A mixture of the above carboxylic acid (106 g.), anhydrous ethanol (100 ml.) and concentrated sulphuric acid (20 ml.) is heated under reflux for 75 hours, cooled, and poured into a mixture of ice and water (1.5 l.). The oily organic phase is separated, the aqueous phase is extracted with light petroleum (b.p. 40°–60° C.), and the combined oil and extract is dried by filtration through phase-separating paper, then evaporated. The residue is fractionally distilled at ambient pressure. After a forerun, which is discarded, the ethyl 2-hydroxy-3,3,3-trifluoro-2-trifluoromethylpropionate (72.2 g.), b.p. 119°–121° C., is collected.

EXAMPLE 2

A mixture of ethyl 2-(4-chlorobenzyloxy)-3,3,3-trifluoro-2-trifluoromethylpropionate (3.65 g.), N-aqueous sodium hydroxide (100 ml.) and ethanol (50 ml.) is stirred at ambient temperature for 2 days, and then evaporated in vacuo. Water is added, and the mixture is washed with ether. The aqueous phase is acidified with concentrated hydrochloric acid and extracted with ether. The extract is dried with sodium sulphate, evaporated, and the residue is crystallised from light petroleum (b.p. 40°–60° C.) to give 2-(4-chlorobenzyloxy)-3,3,3-trifluoro-2-trifluoromethylpropionic acid, m.p. 98°–99° C. (1.42 g.).

EXAMPLE 3

A mixture of 2-(4-chlorobenzyloxy)-3,3,3-trifluoro-2-trifluoromethylpropionitrile (20 g.), potassium hydroxide (25 g.), ethanol (250 ml.) and water (250 ml.) is heated under reflux for 15 minutes. Most of the ethanol is evaporated in vacuo, and the residue is cooled until the precipitated oil solidifies. The solid is filtered off, and is recrystallised from a mixture of ether and light petroleum (b.p. 40°–60° C.) (charcoal) to give 2-(4-chlorobenzyloxy)-3,3,3-trifluoro-2-trifluoromethylpropionamide, m.p. 94°–95° C. (13.9 g.).

The 2-(4-chlorobenzyloxy)-3,3,3-trifluoro-2-trifluoromethylpropionitrile used as starting material may be obtained as follows:-

A mixture of 2-hydroxy-3,3,3-trifluoro-2-trifluoromethylpropionitrile sodium salt (43 g.), 4-chlorobenzyl chloride (25.6 g.) and dimethylformamide (200 ml.) is stirred at ambient temperature for 5 days, then evaporated in vacuo. Water is added to the residue, and the mixture is extracted with 1,2,2-trichloro-1,1,2-trifluoroethane. The extract is dried with sodium sulphate, and evaporated. The residue is distilled to give 2-(4-chlorobenzyloxy)-3,3,3-trifluoro-2-trifluoromethylpropionitrile, b.p. 54°–64° C. at 1 mm. pressure (41.0 g.).

EXAMPLE 4

Ethyl 2-hydroxy-3,3,3-trifluoro-2-trifluoromethylpropionate (54.6 g.) is added dropwise, under nitrogen, at 0° C. during 30 minutes to a stirred mixture of sodium hydride (9.6 g. of 60% oil dispersion from which the oil has been washed with light petroleum) and dimethylformamide (500 ml.). The mixture is stirred at ambient temperature for 1 hour, and then 4-(4-chlorophenyl)-benzyl chloride (43.1 g.) is then added in one lot. The resulting solution is stirred under nitrogen for 120 hours at 30°–35° C., then evaporated in vacuo. The residue is mixed with water, and the mixture is extracted with ether. The ethereal extract is washed with water, dried with sodium sulphate and evaporated. The residue is digested with boiling light petroleum (b.p. 40°–60° C.), the insoluble material is filtered off, and the filtrate is treated with charcoal, filtered, concentrated and cooled. Crops of crystals (42.3 g.) melting in the range 57°–62.5° C. are collected and recrystallised to give ethyl 2-[4-(4-chlorophenyl)benzyloxy]-3,3,3-trifluoro-2-trifluoromethylpropionate, (39.9 g.) m.p. 62°–62.5° C.

The above general procedure is repeated but the 4-(4-chlorophenyl)benzyl chloride is replaced by molar equivalent quantities of:-
  a. 1-chloromethylnaphthalene
  b. 1-chloromethyl-4-chloronaphthalene
  c. 2-chloromethylnaphthalene
  d. 1-chloromethyl-2-methylnaphthalene
  e. 2-chloromethyl-6-chloronaphthalene to give (a) ethyl 2-(1-naphthylmethoxy)-3,3,3-trifluoro-2-trifluoromethylpropionate, (b) ethyl 2-(4-chloro-1-naphthylmethoxy)-3,3,3-trifluoro-2-trifluoromethylpropionate and (c) ethyl 2-(2-naphthylmethoxy)-3,3,3-trifluoro-2-trifluoromethylpropionate respectively as oils, and (d) ethyl 2-(2-methyl-1-naphthylmethoxy)-3,3,3-trifluoro-2-trifluoromethylpropionate, m.p 53°–54.5° C., (50 g.) and (e) ethyl 2-(6-chloro-2-naphthylmethoxy)-3,3,3-trifluoro-2-trifluoromethylpropionate, m.p. 64°–65° C., after chromatography in light petroleum (b.p. 40°–60° C.) on a column of neutral grade I alumina using a mixture of light petroleum (b.p. 40°–60° C.) and ether (19:2) as eluant, and recrystallisation from light petroleum (b.p. 40°–60° C.).

The 2-chloromethyl-6-chloronaphthalene used as starting material may be obtained as follows:-

1.9N-Aqueous sodium hypochlorite solution (924 ml.) is added, dropwise at 50°–60° C. to a stirred suspension of 2-acetyl-6-chloronaphthalene (53.2 g.) in ethanol (420 ml.) during 1 hour. The stirring is continued for 1 hour. The mixture is cooled and treated, dropwise at 38° C., with 40% aqueous sodium hydrogen sulphite solution (ca. 50 ml.) until no unreacted hypochlorite remains, and is then acidified with concentrated hydrochloric acid below 25° C. 6-Chloro-2-naphthoic acid (42 g.) m.p. 279°–286° C. is precipitated and is collected, and may be further purified by recrystallisation from toluene to give material of m.p. 286°–287° C.

A suspension of the 6-chloro-2-naphthoic acid (41.2 g.) in a mixture of methanol (500 ml.) and concentrated sulphuric acid (50 ml.) is heated under reflux for 3 hours, stored at ambient temperature for 3 days, then warmed until a solution is obtained. Water (2 l.) and ether (1 l.) are added. The ethereal layer is separated, and is washed in turn with water, N-aqueous sodium hydroxide, and water, dried with magnesium sulphate, and evaporated to give methyl 6-chloro-2-naphthoate (38.8 g.) m.p. 97°–98° C., which may be further purified by recrystallisation from light petroleum (b.p. 40°–60° C.) to give material of m.p. 100°–101° C.

A solution of the methyl 6-chloro-2-naphthoate (111 g.) in ether (2.5 l.) is added, dropwise below 25° C. under nitrogen, to a stirred mixture of ether (250 ml.) and a 70% solution (250 ml.) of sodium dihydro-bis-(2-methoxyethoxy)aluminate in benzene during 1 hour. The mixture is stirred for a further 30 minutes and 2N-hydrochloric acid (250 ml.) is added cautiously. The solution is decanted from undissolved solid, and concentrated hydrochloric acid is added to the solid until it dissolves. The two solutions thus obtained are combined, and ether (1 l.) and a mixture of ice and water (1 l.) are added. The ethereal layer is separated, and the aqueous phase extracted with ether. The ethereal solutions are combined, washed with water, dried and evaporated to give 6-chloro-2-hydroxymethylnaphthalene (95 g.) which may be further purified by crystallisation from toluene to give material of m.p. 134°–137° C.

Thionyl chloride (99.4 g.) is added dropwise at 0° C. during 1 hour to a stirred suspension of the 6-chloro-2-hydroxymethylnaphthalene (96.3 g.) in a mixture of pyridine (59.0 g.) and chloroform (2 3 l). The mixture is stirred for 1 hour at 20° C., then treated dropwise with methanol (60 ml.) and stored for 18 hours. The solution is washed with water, 3N-hydrochloric acid, and water again, dried with magnesium sulphate and evaporated. The residue is crystallised from light petroleum (b.p. 80°–100° C.) to give 2-chloromethyl-6-chloronaphthalene (101 g.) m.p. 107°–110° C. raised to 110°–111° C. by further crystallisation.

EXAMPLE 5

A mixture of ethyl 2-[4-(4-chlorophenyl)benzyloxy]-3,3,3-trifluoro-2-trifluoromethylpropionate (3.3 g.), N aqueous sodium hydroxide (15 ml.) and ethanol (80 ml.) is stirred at ambient temperature for 18 hours, filtered, and the filtrate is evaporated in vacuo. An aqueous suspension of the residual solid is acidified with concentrated hydrochloric acid. The solid is filtered off, washed with water, dried and crystallised from cyclohexane to give 2-[4-(4-chlorophenyl)benzyloxy]-3,3,3-trifluoro-2-trifluoromethylpropionic acid, m.p. 130°–33° C. (2.5 g.)

EXAMPLE 6

The esters a), b) and c) obtained as oils in the second part of Example 4 are hydrolysed by stirring 40 g. of ester with a solution of potassium hydroxide (6.0 g.) in methanol (300 ml.) and water (30 ml.) at ambient temperature for 17–22 hours. The solution is evaporated in vacuo, the residue mixed with water, and the mixture is washed with ether. The aqueous phase is acidified with concentrated hydrochloric acid, and the resulting emulsion is extracted with ether. The extract is washed with water, dried with sodium sulphate and evaporated. The residue is crystallised from light petroleum (b.p. 40°–60° C.) to give the following acids:

2-(1-naphthylmethoxy)-3,3,3-trifluoro-2-trifluoromethylpropionic acid, m.p. 101° C (14.3 g.)
2-(4-chloro-1-naphthylmethoxy)-3,3,3-trifluoro-2-trifluoromethylpropionic acid, m.p. 118°–121° C. or 105°–106° C. (dimorphic) (20 g.)
2-(2-naphthylmethoxy)-3,3,3-trifluoro-2-trifluoromethylpropionic acid, m.p. 109–112° C (15 g.).

The esters d) and e) obtained in the second part of Example 4 are hydrolysed in the same way but the reaction is continued for only 1½ hours to give 2-(2-methyl-1-naphthylmethoxy)-3,3,3-trifluoro-2-trifluoromethylpropionic acid, m.p. 110° C. (decomp.) and 2-(6-chloro-2-naphthylmethoxy)-3,3,3-trifluoro-2-trifluoromethylpropionic acid, m.p. 133°–134.5° C. respectively.

EXAMPLE 7

A solution of 2-hydroxy-3,3,3-trifluoro-2-trifluoromethylpropionitrile sodium salt (4.3 g.) and 4-(4-chlorophenyl)-benzyl chloride (4.7 g.) in dimethylformamide (25 ml.) is stirred at ambient temperature for 10 days, then diluted with water. During this reaction, 2-[4-(4-chlorophenyl)benzyloxy]-3,3,3-trifluoro-2-trifluoromethylpropionitrile is formed and is subsequently hydrolysed to the corresponding amide. The mixture is extracted with 1,2,2-trichloro-1,1,2-trifluoroethane, and the extract is dried with sodium sulphate, then evaporated. The residue is crystallised from cyclohexane to give 2-[4-(4-chlorophenyl)benzyloxy]-3,3,3-trifluoro-2-trifluoromethylpropionamide, m.p. 123°–124° C. (1.6 g.).

EXAMPLE 8

A stirred suspension of 2-[4-(4-chlorophenyl)benzyloxy]-3,3,3-trifluoro-2-trifluoromethylpropionic acid (750 mg.) in water (10 ml.) is treated dropwise at room temperature with 0.4 N-aqueous sodium hydroxide solution (4.50 ml.). The resultant mixture is warmed briefly to 35° C., cooled, and filtered. The filtrate is washed with ether, refiltered, then evaporated in vacuo. The solid residue is dried in vacuo at 100° C. for 12 hours giving sodium 2-[4-(4-chlorophenyl)-benzyloxy]-3,3,3-trifluoro-2-trifluoromethylpropionate sesquihydrate (0.74 g.) as a solid, which does not melt below 300° C.

EXAMPLE 9

A solution of 2-[4-(4-chlorophenyl)benzyloxy]-3,3,3-trifluoro-2-trifluoromethylpropionic acid (290 mg.) and ethyl nicotinate (106 mg.) in ether (10 ml.) is stored at room temperature for 18 hours, then evaporated. This residual solid is dissolved in a small volume of methylene chloride, and the solution diluted with ether to give the ethyl nicotinate salt of 2-[4-(4-chlorophenyl)benzyloxy]-3,3,3-trifluoro-2-trifluoromethylpropionic acid (301 mg.) m.p. 90°–92° C.

EXAMPLE 10

A solution of 2-[4-(4-chlorophenyl)benzyloxy]-3,3,3-trifluoro-2-trifluoromethylpropionic acid (1.2 g.) in either (20 ml.) is treated at 0° C. with an excess of an ethereal solution of diazomethane. The solution is evaporated, and the residue is recrystallised from light petroleum (b.p. 40°–60° C.) to give methyl 2-[4(4-chlorophenyl)benzyloxy]-3,3,3-trifluoro-2-trifluoromethylpropionate (1.1 g.), m.p. 61.5°–62.5° C.

EXAMPLE 11

Ice-cold aqueous ammonia solution (d, 0.88; 10 ml.) is added to 2-[4-(4-chlorophenyl)benzyloxy]-3,3,3-trifluoro-2-trifluoromethylpropionyl chloride (0.68 g.). The solid product is filtered off, and is crystallised from cyclohexane to give 2-[4-(4-chlorophenyl)benzyloxy]-3,3,3-trifluoro-2-trifluoromethylpropionamide (0.58 g.), m.p. 123°–124° C.

The 2-[4-(4-chlorophenyl)benzyloxy]-3,3,3-trifluoro-2-trifluoromethylpropionyl chloride used as starting material may be obtained as follows:

A mixture of 2-[4-(4-chlorophenyl)benzyloxy]-3,3,3-trifluoro-2-trifluoromethylpropionic acid (3.0 g.), thionyl chloride (3.0 ml.), dimethylformamide (0.16 g.) and benzene (10 ml.) is heated under reflux until the solution becomes turbid (ca. 10 minutes). The mixture is evaporated in vacuo, benzene (10 ml.) is added and the evaporation is repeated. Light petroleum (10 ml., b.p. 40°–60° C.) is added to the residue, and the solution is separated from insoluble oils and evaporated to give 2-[4-(4- chlorophenyl)benzyloxy]-3,3,3-trifluoro-2-trifluoromethylpropionyl chloride (3.07 g.), m.p. 30°–35° C.

EXAMPLE 12

A mixture of 2-diethylaminoethanol (814 mg.) and pyridine (10 ml.) is added at 0° C. to 2-[4-(4-chlorophenyl)benzyloxy]-3,3,3-trifluoro-2-trifluoromethylpropionyl chloride (3.07 g.). The mixture is stirred at room temperature until the acid chloride dissolves, and the solution is stored at 0° C. for 2 days. The mixture is filtered and the filtrate evaporated. The residue is triturated with ether and combined with the solid previously filtered off. The combined solids are crystallised from dioxan-ether to give 2-diethylaminoethyl 2-[4-(4-chlorophenyl)benzyloxy]-3,3,3-trifluoro-2-trifluoromethylpropionate hydrochloride (2.2 g.), m.p. 139°–140° C. (decomposition).

The above procedure is repeated using 3-hydroxymethylpyridine in place of 2-diethylaminoethanol to give 3-pyridylmethyl 2-[4-(4-chlorophenyl)benzyloxy]-3,3,3-trifluoro-2-trifluoromethylpropionate hydrochloride (2.1 g.), m.p. 143°–145° C. (decomposition).

EXAMPLE 13

A solution of 2-[4-(4-chlorophenyl)benzyloxy]-3,3,3-trifluoro-2-trifluoromethylpropionyl chloride (3.10 g.) in tetrahydrofuran (10 ml.) is added dropwise at 0° C. to a stirred mixture of 4-hydroxy-N,N-dimethylbutyramide (885 mg.), triethylamine (773 mg.) and tetrahydrofuran (15 ml.). The mixture is kept at room temperature for 4 hours with stirring, and for 2 days without stirring, then filtered. The filtrate is evaporated, and the residue dissolved in ether. The solution is washed with water, 0.4 N-aqueous sodium hydroxide, N-hydrochloric acid and water again, dried and evaporated to a syrup (3.3 g.). The syrup is dissolved in toluene (10 ml.) and applied to a column of silica gel (90 g.). The column is washed with toluene (700 ml.), and then eluted with ether (900 ml.). The ether is evaporated, and the residue is recrystallised from ether-light petroleum (b.p. 40°–60° C.) to give 3-dimethylcarbamoylpropyl 2-[4-(4-chlorophenyl)benzyloxy]-3,3,3-trifluoro-2-trifluoromethyl-propionate (2.1 g.), m.p. 54°–55° C.

EXAMPLE 14

N,N-Dimethylaniline (467 mg.) in tetrahydrofuran (5 ml.) is added at 10° C. to a stirred mixture of 2-[4-(4-chlorophenyl)benzyloxy]-3,3,3-trifluoro-2-trifluoromethylpropionyl chloride (2.06 g.), 1,3-propanediol (178 mg.), and tetrahydrofuran (10 ml.). The resulting solution is heated under reflux for 2.5 hours, then evaporated in vacuo. The residue is mixed with ether and water, and the ethereal phase is separated, washed with water, 2N-hydrochloric acid, 0.5N-aqueous sodium hydroxide and water again, dried and evaporated. The residue is triturated with light petroleum (b.p. 30°–40° C.), and the solid recrystallised twice from light petroleum (b.p. 60°–80° C.) to give trimethylene bis{2-[4-(4-chlorophenyl)benzyloxy]-3,3,3-trifluoro-2-trifluoromethylpropionate} (0.72 g.), m.p. 93°–94° C.

EXAMPLE 15

A solution of 2-[4-(4-chlorophenyl)benzyloxy]-3,3,3-trifluoro-2-trifluoromethylpropionyl chloride (3.16 g.) in 1,2-dichloroethane (10 ml.) is added, dropwise and below 10° C., to a stirred mixture of 2-(4-chlorophenyloxy)-2-methylpropanol (1.40 g.), pyridine (4.0 ml.), and 1,2-dichloroethane (10 ml.). The mixture is stirred at ambient temperature for 20 hours, then mixed with ice-water and chloroform. The organic phase is separated, and washed with 3N-hydrochloric acid and water. 0.4N-Aqueous potassium hydroxide (5 ml.) and ice are added, the mixture is shaken, and enough ether is added to cause the resulting emulsion to separate into two layers. The organic layer is washed with water, dried and evaporated. The residual oil (3.6 g.) is chromatographed in light petroleum (b.p. 60°–80° C.) on a column of silica gel (45 g.). The column is washed portionwise the solvent (2 l ) until no more material is eluted, and then with a mixture of light petroleum and ether (10:1, 200 ml.). This eluate is evaporated to give 2-(4-chlorophenyloxy)-2-methylpropyl 2-[4-(4-chlorophenyl)benzyloxy]-3,3,3-trifluoro-2-trifluoromethylpropionate (2.6 g.) as a syrup.

EXAMPLE 16

A mixture of (±)-methyl 2-hydroxy-2-trifluoromethylpropionate (17.2 g.) and dimethyl formamide (20 ml.) is added dropwise at 0° C. to a stirred suspension of sodium hydride (4.2 g. of a 60% dispersion in oil from which the oil has been washed with light petroleum) in dimethylformamide (200 ml.). The mixture is stirred at ambient temperature for 1 hour, and then 4-(4-chlorophenyl)benzyl chloride (19.0 g.) is added. The stirring is continued for 4 days, and then the mixture is filtered. The filtrate is evaporated in vacuo, water is added, and the resulting mixture is extracted with ether. The extract is dried with sodium sulphate and evaporated. The residue is repeatedly crystallised from methanol and from cyclohexane giving an impure fraction (26.4 g.) (A) and prisms (3.1 g.) of (±)-methyl 2-[4-(4-chlorophenyl)benzyloxy]-3,3,3-trifluoro-2-methylpropionate, m.p. 83°–85° C.

The above general procedure is repeated except that the 4-(4-chlorophenyl)benzyl chloride is replaced by a molar equivalent quantity of 1-chloromethyl-4-chloronaphthalene, 2-chloromethyl-6-chloronaphthalene, 2-chloromethylnaphthalene or 1-chloromethylnaphthalene to give, respectively (±)-methyl 2-(4-chloro-1-naphthylmethoxy)-3,3,3-trifluoro-2-methylpropionate as an oil (18 g.), (±)-methyl 2-(6-chloro-2-naphthylmethoxy)-3,3,3-trifluoro-2-methylpropionate, m.p. 105°–106° C., (±)-methyl 2-(2-naphthylmethoxy)-3,3,3-trifluoro-2-methylpropionate as a solid or (±)-methyl 2-(1-naphthylmethoxy)-3,3,3-trifluoro-2-methylpropionate as an oil.

EXAMPLE 17

A mixture of the impure ester fraction from the previous example (fraction A) of (±)-methyl 2-[4-(4-chlorophenyl)benzyloxy]-3,3,3-trifluoro-2-methylpropionate (15.7 g.), potassium hydroxide (3.0 g.), methanol (300 ml.) and water (30 ml.) is stirred at ambient temperature for 18 hours. The suspension is filtered, and the filtrate is evaporated. The residue is mixed with water, and the mixture is washed with ether. The aqueous phase is acidified with concentrated hydrochloric acid then extracted with ether. The extract is dried with sodium sulphate and evaporated. The residue is crystallised from cyclohexane and from a mixture of toluene and light petroleum (b.p. 60°–80° C.) to give (±)-2-[4-(4-chlorophenyl)benzyloxy]-3,3,3-trifluoro-2-methylpropionic acid, m.p. 135°–136° C. (5.7 g.). The above process is repeated with (±)-methyl 2-(4-chloro-1-naphthylmethoxy)-3,3,3-trifluoro-2-methylpropionate obtained as an oil in Example 16, to give (±)-2-(4-chloro- 1-naphthylmethoxy)-3,3,3-trifluoro-2-methylpropionic acid, m.p. 120°–121° C. (11.1 g.).

The above process is repeated with (±)-methyl 2-(6-chloro-2-naphthylmethoxy)-3,3,3-trifluoro-2-methylpropionate, (±)-methyl 2-(2-naphthylmethoxy)-3,3,3-trifluoro-2-methylpropionate or (±)-methyl 2-(1-naphthylmethoxy)-3,3,3-trifluoro-2-methylpropionate except that the reaction is carried out for 4½, 2 and 2½ hours respectively to give (±)-2-(6-chloro-2-naphthylmethoxy)-3,3,3-trifluoro-2-methylpropionic acid, m.p. 150°–153° C. (from toluene-cyclohexane), (±)-2-(2-naphthylmethoxy)-3,3,3-trifluoro-2-methylpropionic acid, m.p. 116°–118° C. (from cyclohexane) or (±)-2-(1-naphthylmethoxy)-3,3,3-trifluoro-2-methylpropionic acid, m.p. 82°–84° C. (from light petroleum b.p. 60°–80° C.) respectively.

EXAMPLE 18

A solution of (±)-2-(2-nephthylmethoxy)-3,3,3-trifluoro-2-methylpropionic acid (5.7 g.) or (±)-2-(1-naphthylmethoxy)-3,3,3-trifluoro-2-methylpropionic acid (4.0 g.) in ether (50 ml.) is treated with an excess of ethereal diazomethane at 0° C. The solution is evaporated and the residue recrystallised to give, respectively, (±)-methyl 2-(2-naphthylmethoxy)-3,3,3-trifluoro-2-methylpropionate (3.2 g.) m.p. 65°–67° C. (from light petroleum b.p. 60°–80° C.) or (±)-methyl 2-(1-naphthylmethoxy)-3,3,3-trifluoro-2-methylpropionate (4.1 g.), m.p. 31°–33° C. (from methanol).

EXAMPLE 19

A mixture of ethyl 2-hydroxy-3,3,3-trifluoro-2-trifluoromethylpropionate (2.74 g.) and dimethylformamide (2 ml.) is added, dropwise at 0° C. under nitrogen, to a stirred mixture of sodium hydride (0.48 g. of a 60% oil dispersion from which the oil has been washed with light petroleum) and dimethylformamide (25 ml.). The mixture is stirred at ambient temperature for 30 minutes, and then 4-[4-chlorophenyl]phenoxymethyl chloride (2.30 g.) is added. Stirring is continued for 3 days at 26° C., and the mixture is evaporated in vacuo. The residue is mixed with water, and the mixture is extracted with ether. The extract is washed with water, dried with sodium sulphate, and evaporated. The residue is digested with boiling light petroleum (b.p. 40°–60° C.), insoluble material is filtered off and the filtrate is run through a small column (2 × 1 cm.) of neutral grade I alumina to remove colour. The eluted material is crystallised from light petroleum (b.p. 30°–40° C.) to give ethyl 2-[4-(4-chlorophenyl)phenoxymethoxy]-3,3,3-trifluoro-2-trifluoromethylpropionate, m.p. 42°–43° C. (3.0 g.). The 4-[4-chlorophenyl]phenoxymethyl chloride used as starting material may be obtained as follows:

In a 1-liter round-bottomed flask is placed 4-(4-chlorophenyl)phenol (25.5 g.), 4.0 N aqueous sodium hydroxide (39.0 ml.) and water (75 ml.). The mixture is heated to 90°–100° C., and sodium chloromethyl sulphonate (46.5 g.) is added. The mixture is heated rapidly to 160°–170° C. (bath temperature) while a current of air is passed through the flask. When most of the water has been removed the temperature of the bath is raised to, and kept at, 220°–225° C., for 90 minutes; the mixture is then cooled. The solid cakes obtained from two identical experiments are ground with water (200 ml.) in a mortar. The resulting suspension is heated to 80° C. and allowed to cool slowly, then filtered. The product is washed with water and dried to give sodium 4-(4-chlorophenyl)phenoxymethylsulphonate (58.4 g.) as a cream coloured powder pure enough for use. It may be further purified by crystallisation from aqueous dimethylsulphoxide and obtained as a microcrystalline powder not melting at 300° C.

A mixture of the above crude salt (9.6 g.) and phosphorus pentachloride (12.5 g.) contained in a beaker of 250 ml. capacity is stirred continuously by means of a glass rod while the mixture is heated rapidly to 80°–85° C. (bath temperature). After a few minutes at this temperature a vigorous reaction takes place and soon subsides. Heating at 80°–85° C. is continued for a further 30 seconds, then the mixture is cooled.

The combined product obtained from six identical experiments is mixed with ice and water, and the mixture is extracted with ether. The extract is washed with water, and with saturated aqueous sodium chloride, dried with sodium sulphate and evaporated in vacuo. The residual solid is crystallised from light petroleum (b.p. 60°–80° C.) to give 4-(4-chlorophenyl)phenoxymethyl chloride, m.p. 68°–70° C. (29.5 g.).

EXAMPLE 20

A mixture of ethyl 2-[4-(4-chlorophenyl)phenoxymethoxy]-3,3,3-trifluoro-2-trifluoromethylpropionate (502 mg.) potassium hydroxide (88 mg.), methanol (4 ml.) and water (1 ml.) is stirred at 20° C. for 22 hours, then evaporated in vacuo. The residue is dissolved in water, and the solution is acidified with 3 N-hydrochloric acid. The solid which separates is filtered off. Crystallisation from a mixture of cyclohexane and light petroleum (b.p. 40°–60° C.) gives prisms (204 mg.) of 2-[4-(4-chlorophenyl)phenoxymethoxy]-3,3,3-trifluoro-2-trifluoromethylpropionic acid, m.p. 134°–135° C.

EXAMPLE 21

Ethyl 2-hydroxy-3,3,3-trifluoro-2-trifluoromethylpropionate (24.0 g.) is added dropwise at 0° C. to a stirred suspension of sodium hydride (4.0 g. of a 60% dispersion in oil from which the oil has been washed with light petroleum) in light petroleum (200 ml., b.p. 40°–60° C.). The mixture is stirred at ambient temperature for 15 minutes and di-(4-chlorophenyl)iodonium chloride (38.6 g.) is added. The mixture is stirred thoroughly, and the solvent is evaporated in vacuo. The solid residue is stirred and heated in a bath to 110° C., at which temperature a vigorous reaction occurs, and then for a further 15 minutes at 120° C., then cooled. Light petroleum (b.p. 40°–60° C.) is added, insoluble material is filtered off, and the filtrate is evaporated yielding an oil (53.4 g.).

The crude oil (75.6 g.) obtained from two experiments is chromatographed on a column of silica gel (400 g.) made up in light petroleum (b.p. 40°–60° C.). The column is eluted with portions of solvents, following progress by examining the infra-red spectra of the products obtained by evaporating the eluates. The column is washed with the same solvent (1500 ml.) which elutes 4-chloroiodobenzene. Elution is then continued, using a 19:1 mixture of light petroleum (b.p. 40°–60° C.) and ether. The first 100 ml. of eluate yields a mixed product which is discarded. Continued elution with 700 ml. of the mixed solvent then elutes the product (30.6 g.; I.R. spectral max 1767 cm.$^{-1}$), which is distilled to give ethyl 2-(4-chlorophenoxy)-3,3,3-trifluoro-2-trifluoromethylpropionate, b.p. 122°–123° C. at 23 mm. (23.1 g.).

The above procedure is repeated except that the di-(4-chlorophenyl)iodonium chloride is replaced by a molar equivalent quantity of:

diphenyliodonium chloride,
di-(4-methoxyphenyl)iodonium bromide,
di-(4-fluorophenyl)iodonium chloride, or
di-(1-naphthyl)iodonium mixed bromide and chloride.

In the case of diphenyliodonium chloride, the desired product is eluted from the silica column with a 2:1 mixture of light petroleum and ether, needing a forerun of 1.3 l. and 750 ml. of solvent to elute the product ethyl 2-phenoxy-3,3,3-trifluoro-2-trifluoromethylpropionate, b.p. 102°–104° C. at 23 mm. pressure (32.5 g. from 36.0 g. of ethyl 2-hydroxy-3,3,3-trifluoro-2-trifluoromethylpropionate).

In the case of di-(4-methoxyphenyl)iodonium bromide, the vigorous reaction occurs at 170° C. and the mixture is heated at 180° C. for 10 minutes. The silica column is eluted with a 19:1 mixture of light petroleum and ether throughout, and after a forerun of 1250 ml., a further 1250 ml. of solvent elutes ethyl 2-(4-methoxyphenoxy)-3,3,3-trifluoro-2-trifluoromethylpropionate, b.p. 141°–142° C. at 12 mm. pressure (5.3 g.).

In the case of di-(4-fluorophenyl)iodonium chloride, the vigorous reaction occurs at 104° C. and the mixture is heated at 100°–110° C. for 1 hour. The silica column is washed with light petroleum (b.p. 40°–60° C.) then mixtures of light petroleum and ether (49:1, 600 ml.; 19:1, 300 ml.), and the product is then eluted with 300 ml. of a 10:1 mixture of light petroleum and ether to give ethyl 2-(4-fluorophenoxy)-3,3,3-trifluoro-2-trifluoromethylpropionate, b.p. 92°–94° C. at 12 mm. pressure (4.6 g. from 12 g. of starting ester).

In the case of di-(1-naphthyl)iodonium mixed bromide and chloride, the vigorous reaction occurs at 130° C. and the mixture is heated at 140° C. for 1 hour. The silica column is washed with light petroleum (b.p. 40°–60° C.), and the product eluted with a 19:1 mixture of light petroleum and ether to give ethyl 2-(1-naphthyloxy)-3,3,3-trifluoro-2-trifluoromethylpropionate, b.p. 89°–91° C. at 0.1 mm pressure (8.5 g. from 12 g. of starting ester).

EXAMPLE 22

Ethyl 2-hydroxy-3,3,3-trifluoro-2-trifluoromethylpropionate (12.0 g.) is added dropwise at 0° C. to a stirred suspension of sodium hydride (2.0 g. of a 60% emulsion in oil from which the oil has been wshed with xylene) in xylene (200 ml.). The mixture is stirred at 0° C. for 1.5 hours, and di-(4-chlorophenyl)iodonium chloride (18.7 g.) is added. The stirred suspension is heated under reflux for 1.5 hours, cooled, and filtered. The filtrate is evaporated in vacuo and the residual oil (30.4 g.) is chromatographed on a column of silica (150 g.) in light petroleum (b.p. 40°–60° C.). Elution with the same solvent (750 ml.) elutes 4-chloroiodobenzene. Further elution with the solvent (1000 ml.) and with a mixture of light petroleum and ether (19:1) (1000 ml.) elutes the oily product (14.5 g.) which is fractionally distilled to give ethyl 2-(4-chlorophenoxy)-3,3,3-trifluoro-2-trifluoromethylpropionate (11.7 g.) b.p. 122°–123° C. at 20 mm. pressure.

EXAMPLE 23

Ethyl 2-hydroxy-3,3,3-trifluoro-2-trifluoromethylpropionate (12.0 g.) is added, dropwise at 0° C. under nitrogen, to a stirred mixture of toluene (200 ml.) and sodium hydride (2.0 g. of a 60% dispersion in oil from which the oil has been washed with toluene). The mixture is stirred at ambient temperature for 1.5 hours, and phenyl-2-thienyliodonium trifluoroacetate (20.0 g.) is added. The mixture is heated under reflux with continued stirring for 1 hour, then cooled, and filtered. The filtrate is evaporated in vacuo, and the residual red oil (22.2 g.) is fractionally distilled at 24 mm. pressure to give ethyl 2-phenoxy-3,3,3-trifluoro-2-trifluoromethylpropionate, b.p. 103°–105° C. (9.4 g.).

The above process is repeated except that the phenyl-2-thienyliodonium trifluoroacetate is replaced by a molar equivalent of 4-biphenylyl-2-thienyliodonium chloride and the residual oil is chromatographed on silica gel, washed with light petroleum (b.p. 40°–60° C.; 1.5. l.) and a 99:1 mixture of light petroleum and ether (500 ml.), and eluted with a 50:1 (1.5 l.) and a 20:1 (1.5 l.) mixture of light petroleum and ether. The eluate is evaporated, and the residue distilled to give ethyl 2-(4-biphenylyloxy)-3,3,3-trifluoro-2-trifluoromethylpropionate, b.p. 115°–116° C. at 0.1 mm. pressure (16.5 g. from 15 g. of starting ester).

The 4-biphenylyl-2-thienyliodonium chloride used as starting material may be obtained as follows:

A mixture of thiophene (21.9 g.) and acetic anhydride (150 ml.) is added dropwise at −20° C. to a stirred mixture of (diacetoxyiodo)-4-biphenyl (50 g.), acetic anhydride (125 ml.) and trifluoroacetic acid (37.5 ml.). The mixture is stirred at −20° C. for 2 hours, at −10° C. for 2 hours, and at 0° C. for 18 hours. The mixture is evaporated in vacuo below 40° C., and the residue is washed in turn with water, ether, and light petroleum. The solid is crystallised twice from toluene, and suspended in water (500 ml.). Ethanol (750 ml.) is addd until the solid dissolves, and the solution is poured into a solution of ammonium chloride (15.0 g.) in water (50 ml.). The precipitated solid is filtered off, washed with water, stirred with water (500 ml.) for 2 hours at ambient temperature, then filtered off and washed with water and ether, to give 4-biphenylyl-2-thienyliodonium chloride (35.1 g.), m.p. 209°–210° C.

EXAMPLE 24

Ethyl 2-hydroxy-3,3,3-trifluoro-2-trifluoromethylpropionate (18.0 g.) is added, dropwise at 0° C. under nitrogen, to a stirred mixture of light petroleum (b.p. 60°–80°, 300 ml.) and sodium hydride (3.0 g. of a 60% dispersion in oil from which the oil has been washed with light petroleum). The mixture is stirred for 10 minutes at ambient temperature, and 4-(4-chlorophenyl)phenyl-2-thienyliodonium trifluoroacetate (18.3 g.) is added. The mixture is stirred until well mixed, and is then evaporated in vacuo. The residue is heated in a bath to 110° C. at which temperature a vigorous reaction occurs. When it subsides, toluene (400 ml.) is added and the stirred mixture is heated under reflux for 1 hour, cooled and filtered. The filtrate is evaporated and the residue (41.6 g.) is chromatographed in light petroleum (b.p. 60°–80° C.) on a column of silica gel (400 g.). The column is washed portionwise with a mixture of light petroleum and ether (99:1, 1.5 l.), then eluted with a (49:1) mixture (3.1). The eluate is evaporated to give a solid (23.8 g.) which is crystallised from methanol to give ethyl 2-[4-(4chlorophenyl)phenoxy]-3,3,3-trifluoro-2-trifluoromethylpropionate m.p. 44°–45° C.

The 4-(4-chlorophenyl)phenyl-2-thienyliodonium trifluoroacetate used as starting material may be obtained as follows:

Peracetic acid (40%, 13 ml.) is added dropwise to a stirred suspension of 4-(4-chlorophenyl)iodobenzene (12.6 g.) in acetic acid (25 ml.) at 30° C. during 1hour. The mixture is stirred at 30° C. for 6 hours, and at ambient temperature for 2 days, then evaporated to dryness in vacuo. The residue is washed with light petroleum, and is crystallised from chloroform to give 4-(4-chlorophenyl)-(diacetoxyiodo)-benzene (10.7 g.) m.p. 147°–150° C.

A mixture of thiophene (8.7 g.) and acetic anhydride (60 ml.) is added to a stirred suspension of 4-(4-chlorophenyl)-(diacetoxyiodo)benzene (21.7 g.) in a mixture of acetic anhydride (50 ml.) and trifluoroacetic acid (15 ml.) below −10° C. during 1 hour. The mixture is stirred at −10° C. for 2 hours, at ambient temperature for 18 hours and is then filtered. The filtrate is concentrated to small volume in vacuo, and ether is added. The solid so formed is filtered off and crystallised from toluene to give 4-(4-chlorophenyl)-phenyl-2-thienyliodonium trifluoroacetate (13.7 g.), m.p. 175°–177° C.

EXAMPLE 25

A mixture of ethyl 2-(4-chlorophenoxy)-3,3,3-trifluoro2-trifluoromethylpropionate (14.6 g.), 4.5 N-aqueous potassium hydroxide (19.2 ml.) and methanol (35 ml.) is stirred at ambient temperature for 2¼ hours. The resulting solution is diluted with water and washed with ether. The aqueous phase is acidified with concentrated hydrochloric acid, and extracted with ether. The extract is washed with water, dried with sodium sulphate and evaporated. The residue is sublimed twice at 100° C. and 0.3 mm. pressure, and the sublimate is washed with light petroleum (b.p. 30°–40° C.) to give 2-(4-chlorpheonxy)- 3,3,3-trifluoro-2-trifluoromethylpropionic acid, m.p. 81°–83° C. (5.1 g.). The acid may be further purified by crystallisation (prisms) from light petroleum (b.p. 60°–80° C.) followed by sublimation, which yields material of m.p. 82°–83° C.

The above process is repeated except that the ethyl 2-(4-chlorophenoxy)-3,3,3-trifluoro-2-trifluoromethylpropionate is replaced by ethyl 2-phenoxy-3,3,3-trifluoro-2-trifluoromethylpropionate (13 g.) and the residue obtained by evaporation of the ethereal extract is purified by distillation at 10⁻³ mm. pressure, crystallisation from petrol (b.p. 30°–40° C.) at −65° C. and redistillation to give 2-phenoxy-3,3,3-trifluoro-2-trifluoromethylpropionic acid, b.p. 68°–70° C, at 10⁻³ mm., m.p. 6°–8° c. (8 g.).

The above process is repeated except that the ethyl 2-(4-chlorophenoxy)-3,3,3-trifluoro-2-trifluoromethylpropionate is replaced by ethyl 2-(4-fluorophenoxy)-3,3,3-trifluoro-2-trifluoromethylpropionate (8.6 g.), ethyl 2-(1-naphthyloxy)-3,3,3-trifluoro-2-trifluoromethylpropionate (4.8 g.), ethyl 2-(4-biphenyloxy)-3,3,3-trifluoro-2-trifluoromethylpropionate (1.96 g.) or ethyl 2-[4-(4-chlorophenyl)phenoxy]-3,3,3-trifluoro2-trifluoromethylpropionate (3.35 g.) and the 19.2 ml. of 4.5N-aqueous potassium hydroxide is replaced by an equivalent quantity (based of the amount of starting ester) of 5.2N-aqueous potassium hydroxide. In the case of ethyl 2(1-naphthyloxy)-3,3,3-trifluoro-2-trifluoromethylpropionate, the hydrolysis is continued for 4½ hours. In each case the sublimation step is omitted, and the residue after evaporation of the ethereal extract is crystallised from light petroleum (b.p. 60°–80° C.) to give 2-(4-fluorophenoxy)-3,3,3-trifluoro-2-trifluoromethylpropionic acid, m.p. 77°–78° C. (1.5 g.), 2-(1-naphthyloxy)3,3,3-trifluoro-2-trifluoromethylpropionic acid, m.p. 125°–126° C. (0.46 g.), 2-(4-biphenylyloxy)-3,3,3-trifluoro-2-trifluoromethylpropionic acid, m.p. 137°–138° C. (1.15 g.), or 2-[4-(4-chlorophenyl)phenoxy]-3,3,3-trifluoro-2-trifluoromethylpropionic acid, m.p. 159°–160° C. (1.15 g.), respectively.

EXAMPLE 26

An excess of a solution of diazomethane in ether is added to an ethereal solution of 2-(4-chlorophenoxy)-3,3,3-trifluoro-2-trifluoromethylpropionic acid (0.25 g.) at 0° C. Evaporation of the resulting solution yields methyl 2(4chlorophenoxy)-3,3,3-trifluoro-2-trifluoromethylpropionate (0.25 g.), b.p. (bath temperature) 140° C. at 30 mm. pressure.

The procedure is repeated using as the acid, 2-phenoxy-3,3,3-trifluoro-2-trifluoromethylpropionic acid (0.10 g.) to give methyl 2-phenoxy-3,3,3-trifluoro-2-trifluoromethylpropionate (0.1 g) b.p. (bath temperature) 130° C. at 30 mm. pressure.

EXAMPLE 27

An excess of ice-cold aqueous ammonia (d, 0.88) is added at 0° C. to 2-(4-chlorophenoxy)-3,3,3-trifluoro-2-trifluoromethylpropionyl chloride (151 mg.), and the crystals which separate are collected and recrystallised from a mixture of benzene and light petroleum (b.p. 60°–80° c.) to give 2-(4-chlorophenoxy)-3,3,3-trifluoro-2-trifluoromethylpropionamide (49 mg.), m.p. 77°–79° C.

The acid chloride used as starting material is obtained as follows:-

A mixture of 2-(4-chlorophenoxy)-3,3,3-trifluoro-2-trifluoromethylpropionic acid (161 mg.), thionyl chloride (200 mg.), dimethylformamide (20 mg.) and light petroleum (2 ml. b.p. 40°–60° C.) is heated under reflux for 15 minutes and the solvent evaporated. Light petroleum (5 ml. is added, and the evaporation repeated. The residue is dissolved in light petroleum, the solution filtered and evaporated to give 2-(4-chlorophenoxy)-3,3,3-trifluoro-2-trifluoromethylpropionyl chloride (151 mg.) as an oil.

EXAMPLE 28

(±)-Methyl 2-hydroxy-2-trifluoromethylpropionate (25.8 g.) is added dropwise at 0° C. under nitrogen to a stirred suspension of sodium hydride (6.0 g. of a 60% dispersion in oil from which the oil has been washed with toluene) in toluene (250 ml.). The mixture is stirred at ambient temperature for 30 minutes, and di-(4-chlorophenyl)iodonium chloride (57.9 g.) is added. The stirred suspension is heated under reflux for 1 hour, cooled, and filtered. The filtrate is evaporated in vacuo, and the residual oil (73.1 g.) is chromatographed on a column of silica gel (370 g.) in light petroleum (b.p. 40°–60° C.). The column is washed portionwise with the solvent (2.1 l.), and with a mixture of light petroleum and ether (19:1, 750 ml.). Further washing with the mixed solvent (400 ml.) elutes impure product (2 g.) followed after a further 600 ml. of solvent by the product (22.0 g.). The last fraction is distilled to give (±)-methyl 2-(4-chlorophenoxy)-3,3,3-trifluoro-2-methylpropionate b.p. 117°–120° C. at 12 mm. pressure (15.3 g.).

EXAMPLE 29

A mixture of (±)-methyl 2-(4-chlorophenoxy)-3,3,3-trifluoro-2 -methylpropionate (1.41 g.), methanol (4.0 ml.), and 4.5 N-aqueous potassium hydroxide (2.3 ml.) is stirred at ambient temperature for 10 minutes. The resulting solution is diluted with water, washed with ether, acidified with concentrated hydrochloric acid, and extracted with ether. The extract is washed with water, dried with sodium sulphate and evaporated to a residue which is crystallised from light petroleum (b.p. 60°–80° C.) to give (±)-2-(4-chlorophenoxy)-3,3,3-trifluoro-2-methylpropionic acid, m.p. 141°–142° C. (0.7 g.).

EXAMPLE 30

(±)-Methyl 2-hydroxy-2-trifluoromethylpropionate (8.6 g.) is added dropwise, at 0° C. under nitrogen, to a stirred suspension of sodium hydride (2.0 g. of a 60% dispersion in oil from which the oil has been washed with toluene) is toluene (250 ml.). The mixture is stirred at ambient temperature for 15 minutes, and 4-(4-chlorophenyl)phenyl-2-thienyliodonium trifluoroacetate (25.5 g.) is added. The mixture is stirred and heated under reflux for 1 hour, then cooled and filtered. The filtrate is evaporated, and the residue is digested with ether. The ether is evaporated to give (±)-methyl 2-[4-(4chlorophenyl)phenoxy]-3,3,3-trifluoro-2-methylpropionate as a solid.

EXAMPLE 31

A mixture of (±)-methyl 2-[4-(4-chlorophenyl)-phenoxy]3,3,3-trifluoro-2-methylpropionate (20 g.), methanol (120 ml.) and 5.2 N-aqueous potassium hydroxide (13 ml.) is stirred at ambient temperature for 18 hours. Most of the methanol is evaporated in vacuo, and water is added. The mixture is washed with light petroleum, and concentrated hydrochloric acid added to the aqueous phase. The mixture is extracted with ether, and the extract is dried with sodium sulphate, treated with carbon and evaporated. The residue is crystallised from toluene to give (±)-2[4-(4-chlorophenyl)phenoxy]-3,3,3-trifluoro-2-methylpropionic acid, m.p. 198°–199° C. (8.35 g.).

EXAMPLE 32

A solution of (±)-2-[4-(4-chlorophenyl)phenoxy]-3,3,3-trifluoro-2-methylpropionic acid (3.0 g.) in ether (100 ml.) is treated with an excess of ethereal diazomethane at 0° C. The solvent is evaporated and the residue recrystallised from methanol to give (±)-methyl-2-]4-(4-chlorophenyl)phenoxy]-3,3,3-trifluoro-2-methylpropionate, m.p. 87°–88° C.

EXAMPLE 33

Ice-cold aqueous ammonia (5 ml., d, 0.91) is added to (±)-2-[4-(4-chlorophenyl)phenoxy]-3,3,3-trifluoro-2-methyl propionyl chloride (401 mg.) with stirring. The solid is filtered off, washed with water, dried, and is crystallised from a mixture of benzene and light petroleum (b.p. 60°–80° C.) to give (±)-2-[4-(4-chlorophenyl)phenoxy]-3,3,3-trifluoro-2-methylpropionamide, m.p. 141°–142° C. (342 mg.).

The acid chloride used as starting material may be obtained as follows:

A solution of (±)-2-[4-(4-chlorophenyl)phenoxy]-3,3,3-trifluoro-2-methylpropionic acid (414 mg.), thionyl chloride (1.0 g.) and dimethylformamide (0.05 g.) in benzene (10 ml.) is heated under reflux for 1 hour. The solvent is evaporated in vacuo, and light petroleum (10 ml., b.p. 60°–80° C.) is added, and the mixture is re-evaporated. A further 10 ml. of light petroleum are added, and the mixture re-evaporated. The residue is dissolved in light petroleum, and the solution is filtered and evaporated to give (±)-2-[4-(4-chlorophenyl)-phenoxy]-3,3,3-trifluoro-2-methylpropionyl chloride (401 mg.).

EXAMPLE 34

A mixture of (±)-methyl 2-hydroxy-3,3,3-trifluoropropionate (7.9 g.) in toluene (150 ml.) is added, dropwise at 0° C. under nitrogen, to a stirred mixture of toluene (200 ml.) and sodium hydride (2.0 g. of a 60% dispersion in oil from which the oil has been washed with toluene). The mixture is stirred at ambient temperature for 1 hour, 4-(4-chlorophenyl)-phenyl-2-thienyliodonium trifluoroacetate (25.5 g.) is added, and the mixture is heated under reflux for 1 hour with continued stirring, then cooled and filtered from unreacted iodonium salt. The residue obtained by evaporating the filtrate is treated with ether, the mixture is filtered and the filtrate is evaporated. The residue is triturated with three 100 ml. portions of light petroleum and the extracts set aside. The residue is extracted with ether, and the solution filtered. The filtrate is evaporated, and the residue crystallised from ethanol. The mother liquors are evaporated, and the residue is chromatographed in light petroleum (b.p. 60°–80° C.) on a column of silica gel (150 g.). The column is eluted, portionwise, with a mixture of light petroleum and ether (100:1; 1250 ml.) and then with a 50:1 mixture (1300 ml.) and a 25:1 mixture (250 ml.). The last fraction is evaporated, and the residue combined with a solid which separates from the in initial light petroleum extracts. The combined material is crystallised from methanol and from light petroleum (b.p. 80°–100° C.) to give (±)-methyl 2-[4-(4-chlorophenyl)phenoxy]-3,3,3-trifluoropropionate, m.p. 104°–105° C. (1.8 g.).

The (±)-methyl 2-hydroxy-3,3,3-trifluoropropionate used as starting material may be obtained as follows:

A mixture of (±)-2-hydroxy-3,3,3-trifluoropropionic acid (7.8 g.), methanol (10 ml.) and concentrated sulphuric acid (0.5 ml.) is heated under reflux for 2 days. The cooled solution is poured into water (100 ml.), the mixture is saturated with sodium sulphate, and is extracted three times with ether. The extract is dried with sodium sulphate and evaporated. The residual oil (8.6 g.) is fractionally distilled to give (±)-methyl 2-hydroxy-3,3,3-trifluoropropionate b.p. 60°–64° C. at 12 mm. pressure, m.p. 50°–53° C. (3.9 g.).

EXAMPLE 35

A solution of 2-[4-(4-chlorophenyl)benzyloxy]-3,3,3-trifluoro-2-trifluoromethylpropionic acid (2.06 g.) in dimethylformamide (10 ml.) is added dropwise at 0° C. under argon to a stirred suspension of sodium hydride (216 mg. of a 60% dispersion in oil from which the oil has been washed with light petroleum) in dimethylformamide (15 ml.). The mixture is heated at 100° C. for 18 hours, cooled, and evaporated in vacuo. The residue is mixed with water and the solid obtained (1.8 g.) is washed with water and dried, then chromatographed in toluene on a column of silica (60 g.). The column is washed with toluene (900 ml.) until no more material is eluted, and then with ether. The ether is evaporated and the solid (0.4 g.) is crystallised from light petroleum to give (±)-N,N-dimethyl-2-[4-(4-chlorophenyl)-benzyloxy]-3,3,3-trifluoropropionamide, m.p. 103°–107° C. (212 mg.).

EXAMPLE 36

A mixture of (±)-2-[4-(4-chlorophenyl)benzyloxy]-3,3,3-trifluoro-2-methylpropionic acid (0.36 g.), N aqueous sodium hydroxide (1.0 ml.) and water (3.0 ml.) is stirred until no more of the acid dissolves. The mixture is filtered, the filtrate is washed with ether and evaporated in vacuo. The residue is crystallised from a mixture of ethyl acetate and light petroleum (b.p. 60°–80° C.) to give (±)-sodium 2-[4-(4-chlorophenyl)benzyloxy]-3,3,3-trifluoro-2-methylpropionate (0.3 g.) m.p. 271°–272° C. (decomposition).

EXAMPLE 37

A solution of (±)-2-(2-naphthylmethoxy)-3,3,3-trifluoro-2-methylpropionyl chloride (1.3 g.) in ether (10 ml.) is added to a mixture of ammonia (d, 0.90; 10 ml.) and water (100 ml.). The mixture is shaken, and the ether is evaporated. The solid is filtered off and crystallised from light petroleum (b.p. 100°–120° C.) to give (±)-2-(2-naphthylmethoxy)-3,3,3-trifluoro-2-methylpropionamide (0.76 g.) m.p. 111°–112° C.

The (±)-2-(2-naphthylmethoxy)-3,3,3-trifluoro-2-methylpropionyl chloride used as starting material is obtained as follows:

A solution of (±)-2-(2-naphthylmethoxy)-3,3,3-trifluoro-2-methylpropionic acid (6.0 g.), thionyl chloride (7.5 ml.) and dimethylformamide (0.2 g.) in benzene (50 ml.) is heated under reflux for 10 minutes. The mixture is evaporated, benzene (20 ml.) is added and the evaporation repeated twice. Light petroleum (b.p. 40°–60° C., 150 ml.) and carton are added to the residue, and the solution is filtered and evaporated to give (±)-2-(2-naphthylmethoxy)-3,3,3-trifluoro-2-methylpropionyl chloride (5.35 g.) m.p. 39°–43° C.

EXAMPLE 38

A solution of (±)-2-(2-naphthylmethoxy)-3,3,3-trifluoro-2-methylpropionyl chloride (3.0 g.) in ether (20 ml.) is added dropwise at ambient temperature to a stirred solution of 2-diethylaminoethanol (3.0 ml.) in ether (100 ml.). The mixture is stored for 18 hours, filtered, and the solid is washed with ether. The filtrate and washings are evaporated to an oil (3.5 g.), which is dissolved in ether and run through a column of silica gel made up in ether. The column is eluted with 200 ml. of ether, and the eluate evaporated to give 2.4 g. of an oil which is similarly passed through a column of alumina (Neutral, Grade I, 30 g.). Elution with ether yields (±)-2-diethylaminoethyl 2-(2-naphthylmethoxy)-3,3,3-trifluoro-2-methylpropionate (1.05 g.) as an oil.

EXAMPLE 39

A solution of (±)-2-(2-naphthylmethoxy)-3,3,3-trifluoro-2-methylpropionyl chloride (4.3 g.) in benzene (20 ml.) is added, dropwise below 10° C., to a stirred solution of 3-pyridylmethanol (1.20 g.) and pyridine (1.10 g.) in benzene (20 ml.) and light petroleum (5 ml. b.p. 40°–60° C.). The mixture is stirred at 5° C. for 1 hour, and at ambient temperature for 18 hours. The mixture is filtered. The filtrate is diluted with ether, washed with water, aqueous sodium carbonate and water, dried with sodium sulphate, and evaporated to give an oil (4.1 g.). The oil is dissolved in a mixture of ethyl acetate, ethanol, and triethylamine (200:1:1) and is chromatographed on a column of silica gel (210 g.) made up in the same solvent. The column is eluted portionwise with the solvent. The first 350 ml. elutes an impurity (0.1 g.). The following 420 ml. of eluant is evaporated to give (±)-3-pyridylmethyl-2-(2-naphthylmethoxy)-3,3,3-trifluoro-2-methylpropionate (3.9 g.) as a syrup.

EXAMPLE 40

A solution of (±)-2-(2-naphthylmethoxy)-3,3,3-trifluoro-2-methylpropionyl chloride (3.0 g.) in tetrahydrofuran (70 ml.) is added, dropwise at 0° C., to a stirred solution of 4-hydroxy-N,N-dimethylbutyramide (1.20 g.) and triethylamine (2.1 g.) in tetrahydrofuran (35 ml.). The mixture is stored for two days. The solid is filtered off and washed with ether, and the filtrate and washings are evaporated. The residue is dissolved in ether and the solution is washed with water, 0.4 N aqueous sodium hydroxide, and water, dried with magnesium sulphate, and evaporated. The residue is crystallised from a mixture of light petroleum (b.p. 40°–60° C.) and ether to give (±)-3-dimethylcarbamoylpropyl 2-(2-naphthylmethoxy)-3,3,3-trifluoro-2-methylpropionate (1.3 g.) m.p. 42°–43° C.

EXAMPLE 41

A solution of N,N-dimethylaniline (0.90 g.) in tetrahydrofuran (10 ml.) is added dropwise, below 5° C., to a stirred solution of (±)-21-(2-naphthylmethoxy)-3,3,3-trifluoro-2-methylpropionyl chloride (2.2 g.) and 1,3-dihydroxypropane (0.25 g.) in tetrahydrofuran (10 ml.). The mixture is stirred at ambient temperature for 18 hours, and then a further 0.3 g. of the acid chloride and 0.12 g. of N,N-dimethylaniline are added. The mixture is stirred and heated under reflux for 2 hours, and then evaporated in vacuo. The residue is partitioned between ether and water, and the ethereal layer is washed with 3N hydrochloric acid, water 0.4 N aqueous sodium hydroxide, and water, dried with sodium sulphate, and evaporated. The residual oil (1.6 g.) is dissolved in ether and the solution applied to a column of silica gel. (20 g.). The column is eluted with ether (10 ml., which is discarded and then 25 ml.), and the eluate evaporated to give (±)-trimethylene bis[2-(2 naphthylmethoxy)3,3,3-trifluoro-2-methylpropionate ] (0.60 g.), as a syrup.

EXAMPLE 42

A solution of (−) ephedrine (4.15 g.) in ether (100 ml.) is added to a solution of (±)-2-[4-(4-chlorophenyl)-benzyloxy]-3,3,3-trifluoro-2-methylpropionic acid (9.00 g.) in ether (100 ml.). After 18 hours the crystalline salt is filtered off and washed with ether. The filtrate and washings are retained (A). The crystalline salt (4.7 g., m.p. 161°–167° C., $[\alpha]_D^{25}$ −13°; c, 2.3 in methanol) thus obtained is crystallised three times from toluene to give salt (B), and combined mother-liquors (C). Salt (B) (2.5 g., m.p. 169°–170° C. $[\alpha]_D^{25}$ −11°; c, 1.8 in methanol) is shaken for 2 minutes with ether (200 ml.) and 2N aqueous hydrochloric acid (150 ml.). The ethereal layer is separated, and is washed with water, dried with sodium sulphate, and evaporated to give the free acid (1.3 g., m.p. 125°–127° C. $[\alpha]_D^{25}$ + 2.3°; c, 2.2 in methanol), which is recrystallised twice from light petroleum (b.p. 80°–100° C.) to give (±)-2-[4-(4-chlorophenyl)-benzyloxy]-3,3,3-trifluoro-2-methylpropionic acid as prisms (0.90 g.), m.p. 124°–125° C., $[\alpha]_D^{25}$ + 1.7°; c, 1.7 in methanol.

The above mother-liquors (A and C) are combined and evaporated. The residual salts are converted into the corresponding free acid (4.4 g., $[\alpha]_D^{25}$ −0.4°; c 1.9 in methanol), as described for salt (B). Racemic acid (5.70 g.) is added (total 10.10 g.), and this material in ether (100 ml.) is treated with a solution of (±)-ephedrine (4.65 g.) in ether (100 ml.). After three hours, the separated salt is collected and is crystallised three times from toluene to give a salt (4.6 g., m.p. 169°–171° C., $[\alpha]_D^{25} + 11°$; c, 1.9 in methanol). This salt is converted into the free acid (3.1 g., m.p. 124°–125° C., $[\alpha]_D^{25} - 1.7°$; c, 2.1 in methanol) as described for salt (B), and the acid is crystallised once from cyclohexane and once from light petroleum (b.p. 80°–100° C.) to give (−)-2-[4-(4-chlorophenyl)-benzyloxy]-3,3,3-trifluoro-2-methylpropionic acid as prisms (1.7 g.), m.p. 124°–125° C., $[\alpha]_D^{25} - 1.85°$; c, 1.8 in methanol.

EXAMPLE 43

The process of Example 16 is repeated except that he 4-(4-chlorophenyl)benzyl chloride is replaced by a molar equivalent quantity of 2-chloromethyl-6-methoxynaphthalene to give (±)-methyl 2-(6-methoxy-2-naphthylmethoxy)-3,3,3-trifluoro-2-methylpropionate as an oil.

The 2-chloromethyl-6-methoxynaphthalene used as starting material is obtained from methyl 6-methoxy-2-naphthoate by reaction with sodium dihydro-bis-(2-methoxyethoxy)aluminate to give 2-hydroxymethyl-6-methoxynaphthalene, m.p. 118°–120° C. and reaction with thionyl chloride to give 2-chloromethyl-6-methoxynaphthalene, m.p. 63°–65° C. by the general procedure described in Example 4 for the preparation of 2-chloromethyl-6-chloronaphthalene.

EXAMPLE 44

The process of Example 17 is repeated using (±)-methyl 2-(6-methoxy-2-naphthylmethoxy)-3,3,3-trifluoro-2-methylpropionate, obtained as an oil in Example 43, as starting material except that the potassium hydroxide is replaced by 4.4 N aqueous sodium hydroxide and the reaction is carried out for 2½ hours to give (±)-2-(6-methoxy-2-naphthylmethoxy)-3,3,3-trifluoro-2-methylpropionic acid, m.p. 117°–119° C. (from light petroleum b.p. 60°–80° C.).

EXAMPLE 45

A solution of (±)-2-(6-methoxy-2-naphthylmethoxy)-3,3,3-trifluoro-2-methylpropionic acid (1.0 g.) in ether is treated with diazomethane by the process described in Example 18 to give (±)-methyl 2-(6-methoxy-2-naphthylmethoxy)-3,3,3-trifluoro-2-methylpropionate (0.8 g.) m.p. 60°–62° C. (from methanol at −50° C.).

EXAMPLE 46

The process described in Example 30 is repeated except that the 4-(4-chlorophenyl)phenyl-2-thienyliodonium trifluoroacetate is replaced by a molar equivalent quantity of 4-phenoxyphenyl-2-thienyliodonium chloride. The product is obtained as an oil which is dissolved in light petroleum (b.p. 60°–80° C.) and applied to a column of silica gel (500 g.) made up in the same solvent. The column is washed with light petroleum (750 ml.) and mixtures of light petroleum and ether (100:1, 500 ml; 50:1, 2750 ml.) and then eluted with a 10:1 mixture of light petroleum and ether (1000 ml.). The eluate is evaporated and the residue distilled to give (±)-methyl 2-(4-phenoxyphenoxy)-3,3,3-trifluoro-2-methylpropionate (18.1 g.), b.p. 154°–160° C. at 0.05 mm. pressure.

EXAMPLE 47

A mixture of (±) methyl 2-(4-phenoxyphenoxy)-3,3,3-trifluoro-2-methylpropionate (10.2 g.), obtained as in Example 46, methanol (50 ml.) and 4.4 N aqueous sodium hydroxide (7.0 ml.) is stirred at ambient temperature for 2½ hours. The hydrolysis product is then isolated as described in Example 31 to give (±)-2-(4-phenoxyphenoxy)-3,3,3-trifluoro-2-methylpropionic acid (6.4 g.), m.p. 111°–112° C. (from cyclohexane).

EXAMPLE 48

A solution of (±)-2-(4-phenoxyphenoxy)-3,3,3-trifluoro-2-methylpropionic acid (6.4 g.) in ether is treated with an excess of ethereal diazomethane at 0° C. The solution is evaporated and the residue distilled to give (±)-methyl 2-(4-phenoxyphenoxy)-3,3,3-trifluoro-2-methylpropionate (3.3 g.), b.p. 187° C. at 0.1 mm. pressure.

EXAMPLE 49

2-[4-(4-chlorophenyl)benzyloxy]-3,3,3-trifluoro-2-methylpropionic acid (200 g.) is thoroughly mixed with lactose (400 g.) and 10% w/v aqueous gelatin solution (9 g.). The mixture is granulated and the granules mixed with maize starch (35 g.) followed by magnesium stearate (6 g.). The mixture is then compressed into tablets containing 50, 100 or 250 mg. of active ingredient.

The 2-[4-(4-chlorophenyl)benzyloxy]-3,3,3-trifluoro-2-methylpropionic acid may be replaced by a salt thereof or any compound of formula I described in any of Examples 1-48 which is a solid at room temperature.

EXAMPLE 50

Methyl 2-[4-(4-chlorophenyl)benzyloxy]-3,3,3-trifluoro-2-methylpropionate is filled into soft gelatin capsules each containing either 250 mg. or 500 mg. of active ingredient.

The active ingredient may be replaced by any compound of formula I described in any of Examples 1-48 and, if desired, the active ingredient may include a diluent.

What we claim is:

1. A fluorinated compound of the formula:-

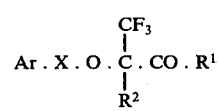

I wherein Ar is a phenyl or naphthyl radical which, may optionally bear as substituent a halogen atom, an alkyl radical of 1–4 carbon atoms or an alkoxy radical of 1–4 carbon atoms, or a phenyl or phenoxy radical which may itself bear as substituent a halogen atom, an alkyl radical or 1–4 carbon atoms or an alkoxy radical of 1–4 carbon atoms; X is —CH₂—; R¹ is a hydroxy radical or an alkoxy radical of 1–6 carbon atoms; and R² is a hydrogen atom, a methyl radical or a trifluoromethyl radical; or, for a compound wherein R¹ is a hydroxy radical, a pharmaceutically acceptable base addition salt thereof.

2. A compound as claimed in claim 1 wherein Ar is a phenyl or naphthyl radical which may optionally bear as substituent a fluorine, chlorine, bromine or iodine atom, or a methyl or methoxy radical or a phenyl or phenoxy radical optionally bearing a fluorine, chlorine, bromine or iodine atom or a methyl or methoxy radical; $R^1$ is a hydroxy radical or an alkoxy radical of 1–6 carbon atoms and $R^2$ is a hydrogen atom, a methyl radical or trifluoromethyl radical.

3. A pharmaceutically acceptable base addition salt as claimed in claim 1 which is an alkali metal or alkaline earth metal salt, or an aluminum salt or a salt with an organic base.

4. A compound as claimed in claim 1 wherein $R^2$ is other than a trifluoromethyl radical which is in an optically active form.

5. A compound as claimed in claim 1 selected from the group consisting of 2-[4-(4-chlorophenyl)benzyloxy]-3,3,3-trifluoro-2-methylpropionic acid and the pharmaceutically acceptable base addition salts thereof.

6. A compound as claimed in claim 1 selected from the group consisting of 2-(4-chloro-1-naphthylmethoxy)-3,3,3-trifluoro-2-methylpropionic acid and the pharmaceutically acceptable base addition salts thereof.

7. A compound as claimed in claim 1 selected from the group consisting of 2-(2-naphthylmethoxy)-3,3,3-trifluoro-2-methylpropionic acid and the pharmaceutically acceptable base addition salts thereof.

8. A compound as claimed in claim 1 selected from the group consisting of 2-(1-naphthylmethoxy)-3,3,3-trifluoro-2-methylpropionic acid and the pharmaceutically acceptable base addition salts thereof.

* * * * *